US006649377B1

US 6,649,377 B1

(12) United States Patent
Allard et al.

(10) Patent No.: US 6,649,377 B1
(45) Date of Patent: Nov. 18, 2003

(54) HUMAN AGGRECANASE AND NUCLEIC ACID COMPOSITIONS ENCODING THE SAME

(75) Inventors: John David Allard, Cupertino, CA (US); Renu Anand Heller, Stanford, CA (US); Paul Klonowski, Cambridge, MA (US); Harold Edgar VanWart, Los Altos, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/568,559

(22) Filed: May 9, 2000

Related U.S. Application Data

(60) Provisional application No. 60/133,343, filed on May 10, 1999.

(51) Int. Cl.[7] .......................... C12P 21/04; C12N 15/00; C12N 15/09; C12N 15/63; C12N 15/70
(52) U.S. Cl. .................... 435/70.1; 435/320.1; 435/325; 536/23.1; 536/23.5
(58) Field of Search ............................. 536/23.1, 23.5; 435/320.1, 325, 70.1; 754/44

(56) References Cited

U.S. PATENT DOCUMENTS

| | | | |
|---|---|---|---|
| 5,427,954 A | 6/1995 | Sandy et al. | 436/89 |
| 5,872,209 A | 2/1999 | Bartnik et al. | 530/324 |

FOREIGN PATENT DOCUMENTS

| | | |
|---|---|---|
| EP | 0 874 050 A2 | 10/1998 |
| WO | WO 97/18207 | 5/1997 |
| WO | WO 98/55643 | 10/1998 |
| WO | WO 98/51665 | 11/1998 |
| WO | WO 9856804 | * 12/1998 |
| WO | WO 99/09000 | 2/1999 |

OTHER PUBLICATIONS

Ngo et al.; Computational Complexity, Protein Structure Prediction, and the Levinthal Paradox, 1994, The Protein folding Problem and Tertiary Structure Prediction: 491–495.*
Rudinger; Characteristics of the amino acids as components of a peptide hormone sequence, 1976, Peptide Hormones: 1–7.*
WF Anderson, Nature, " Human Gene Therapy," Apr.1998, vol. 392, pp. 25–30.*
IM Verma et al., Nature, "Gene therapy–promises, problems and prospects," Sep. 1997, vol. 389, pp. 239–242.*
E Lazar et al., Molecular and Cellular Biology, "Transforming Growth Factor alpha: Mutation of Aspartic Acid 47 and Leucine 48 Results in Different Biological Acitivites," Mar. 1988, vol. 8, No. 3, pp. 1247–1252.*
JU Bowie et al., Science, "Deciphering the Message in Protein Sequences: Tolerance to Amino Acid Substitutions," Mar. 1990, vol. 247, pp. 1306–1310.*

WH Burgess et al., Journal of Cell Biology, "Possible Dissociation of the Heparin–binding and Mitogenic Activities of Heparin–binding (Acidic Fibroblast) Growth Factor 1 . . . Of a Single Lysine Reside," Nov. 1990, vol. 111, pp. 2129–2138.*
K Kuno et al., Journal of Biological Chemistry, " Molecular Cloning of a Gene Encoding a New Type of Metalloproteinase–disintegrin Family Protein with Thrombospondin Motifs as an Inflammation Associated Gene," Jan. 1997, vol. 272, No. I,pp. 556–562.*
Locus Bank, Accession No. AF 149118.*
Zudenka et al., Lucas bank, Accession No. E29406.*
Kuno et al., Lucas Bank, Accession No. D67076.*
Arner et al. (1998). "Cytokine–induced cartilage proteoglycan degradation is mediated by aggrecanase" *Osteoarthritis Cartilage*, vol. 6(3): 214–228.
Arner et al. (1999). "Generation and Characterization of Aggrecanase. A soluble, cartilage–derived aggrecan–degrading activity" *J. Biol. Chem.*, vol. 274(10): 6594–6601.
Billington et al. (1998). "An aggrecan–degrading activity associated with chondrocyte membranes" *Biochem J.*, vol. 336(Pt 1): 207–212.
Buttner et al. (1998). "Membrane type 1 matrix metalloproteinase (MT1–MMP) cleaves the recombinant aggrecan substrate rAgg1mut at the 'aggrecanase' and the MMP sites. Characterization of MT1–MMP catabolic activities on the interglobular domain of aggracan" *Biochem J.*, vol. 333(Pt 1):159–165.
Hughes et al. (1998). "Differential expression of aggrecanase and matrix metalloproteinase activity in chondrocytes isolated from bovine and porcine articular cartilage" *J. Biol. Chem.*, vol. 273(46): 30576–30582.
Ilic et al. (1998). "Characterization of aggrecan retained and lost from the extracellular matrix of atricular cartilage. Involvement of carboxyl–terminal processing in the catabolism of aggrecan" *J. Biol. Chem.*, vol. 273(28): 1751–17458.
Vankemmelbeke et al. (1999). "Coincubation of bovine synovial or capsular tissue with cartilage generates a soluble 'Aggrecanase' activity" *Biochem. Biophys. Res. Commun.*, vol. 255(3): 686–691.

* cited by examiner

*Primary Examiner*—Peter Paras
(74) *Attorney, Agent, or Firm*—Rohan Peries; Robert C. Hall

(57) ABSTRACT

Human aggrecanase and polypeptides related thereto, as well as nucleic acid compositions encoding the same, are provided. The subject polypeptides and nucleic acid compositions find use in a variety of applications, including research, diagnostic, and therapeutic agent screening applications. Also provided are methods of inhibiting aggrecanase activity in a host and methods of treating disease conditions associated with aggrecanase activity, e.g. rheumatoid arthritis, osteo-arthritis, infectious arthritis, gouty arthritis, psoriatic arthritis, spondolysis, sports injury, joint trauma, pulmonary disease, fibrosis, and the like.

5 Claims, 9 Drawing Sheets

FIG. 1i

```
     tgctccaatgcagcgatctgtgcccgaggggttcggaaggcgcaagctgggcagcgacat
  1  ------------+---------+---------+---------+---------+---------+ 60
     acgaggttacgtcgctagacacgggctccccaagccttccgcgttcgacccgtcgctgta
b                                                              M  - ggggaacgcggagcgggctccggggtctcggagctttgggcccgtacccacgctgctgct
 61  ------------+---------+---------+---------+---------+---------+ 120
     ccccttgcgcctcgcccgaggccccagagcctcgaaacccgggcatgggtgcgacgacga
b      G  N  A  E  R  A  P  G  S  R  S  F  G  P  V  P  T  L  L  L  - gctcgccgcggcgctactggccgtgtcggacgcactcgggcgcccctccgaggaggacga
121  ------------+---------+---------+---------+---------+---------+ 180
     cgagcggcgccgcgatgaccggcacagcctgcgtgagcccgcggggaggctcctcctgct
b      L  A  A  A  L  L  A  V  S  D  A  L  G  R  P  S  E  E  D  E  - ggagctagtggtgccggagctggagcgcgccccgggacacgggaccacgcgcctccgcct
181  ------------+---------+---------+---------+---------+---------+ 240
     cctcgatcaccacggcctcgacctcgcgcggggccctgtgccctggtgcgcggaggcgga
b      E  L  V  V  P  E  L  E  R  A  P  G  H  G  T  T  R  L  R  L  - gcacgcctttgaccagcagctggatctggagctgcggcccgacagcagcttttggcgcc
241  ------------+---------+---------+---------+---------+---------+ 300
     cgtgcggaaactggtcgtcgacctagacctcgacgccgggctgtcgtcgaaaaaccgcgg
b      H  A  F  D  Q  Q  L  D  L  E  L  R  P  D  S  S  F  L  A  P  - cggcttcacgctccagaacgtggggcgcaaatccgggtccgagacgccgcttccggaaac
301  ------------+---------+---------+---------+---------+---------+ 360
     gccgaagtgcgaggtcttgcaccccgcgtttaggcccaggctctgcggcgaaggcctttg
b      G  F  T  L  Q  N  V  G  R  K  S  G  S  E  T  P  L  P  E  T  - cgacctggcgcactgcttctactccggcaccgtgaatggcgatcccagctcggctgccgc
361  ------------+---------+---------+---------+---------+---------+ 420
     gctggaccgcgtgacgaagatgaggccgtggcacttaccgctagggtcgagccgacggcg
b      D  L  A  H  C  F  Y  S  G  T  V  N  G  D  P  S  S  A  A  A  - cctcagcctctgcgagggcgtgcgcggcgccttctacctyctgggggaggcgtatttcat
```

FIG. 1ii

```
      421 ---------+---------+---------+---------+---------+---------+ 480
          ggagtcggagacgctcccgcacgcgccgcggaagatggacgaccccctccgcataaagta b          L  S  L  C  E  G  V  R  G  A  F  Y  L  L  G  E  A  Y  F  I  - ccagccgctgcccgccgccagcgagcgcctcgccaccgccgccccaggggagaagccgcc
      481 ---------+---------+---------+---------+---------+---------+ 540
          ggtcggcgacgggcggcggtcgctcgcggagcggtggcggcggggtccctcttcggcgg b          Q  P  L  P  A  A  S  E  R  L  A  T  A  A  P  G  E  K  P  P  - ggcaccactacagttccacctcctgcggcggaatcggcagggcgacgtcggcggcacgtg
      541 ---------+---------+---------+---------+---------+---------+ 600
          ccgtggtgatgtcaaggtggaggacgccgccttagccgtcccgctgcagccgccgtgcac b          A  P  L  Q  F  H  L  L  R  R  N  R  Q  G  D  V  G  G  T  C  - cggggtcgtggacgacgagccccggccgactgggaaagcggagaccgaagacgaggacga
      601 ---------+---------+---------+---------+---------+---------+ 660
          gccccagcacctgctgctcggggccggctgacccttcgcctctggcttctgctcctgct b          G  V  V  D  D  E  P  R  P  T  G  K  A  E  T  E  D  E  D  E  - agggactgagggcgaggacgaaggggctcagtggtcgccgcaggacccggcactgcaagg
      661 ---------+---------+---------+---------+---------+---------+ 720
          tccctgactcccgctcctgcttccccgagtcaccagcggcgtcctgggccgtgacgttcc b          G  T  E  G  E  D  E  G  A  Q  W  S  P  Q  D  P  A  L  Q  G  - cgtaggacagcccacaggaactggaagcataagaaagaagcgatttgtgtccagtcaccg
      721 ---------+---------+---------+---------+---------+---------+ 780
          gcatcctgtcgggtgtccttgaccttcgtattctttcttcgctaaacacaggtcagtggc b          V  G  Q  P  T  G  T  G  S  I  R  K  K  R  F  V  S  S  H  R  - ctatgtggaaaccatgcttgtggcagaccagtcgatggcagaattccacggcagtggtct
      781 ---------+---------+---------+---------+---------+---------+ 840
          gatacacctttggtacgaacaccgtctggtcagctaccgtcttaaggtgccgtcaccaga b          Y  V  E  T  M  L  V  A  D  Q  S  M  A  E  F  H  G  S  G  L  - aaagcattaccttctcacgttgttttcggtggcagccagattgtacaaacaccccagcat
      841 ---------+---------+---------+---------+---------+---------+ 900
          tttcgtaatggaagagtgcaacaaaagccaccgtcggtctaacatgtttgtggggtcgta
```

FIG. 1iii

```
b        K   H   Y   L   L   T   L   F   S   V   A   A   R   L   Y   K   H   P   S   I    - tcgtaattcagttagcctggtggtggtgaagatcttggtcatccacgatgaacagaaggg
    901  ---------+---------+---------+---------+---------+---------+  960
         agcattaagtcaatcggaccaccaccacttctagaaccagtaggtgctacttgtcttccc b        R   N   S   V   S   L   V   V   V   K   I   L   V   I   H   D   E   Q   K   G    - gccggaagtgacctccaatgctgccctcactctgcggaacttttgcaactggcagaagca
    961  ---------+---------+---------+---------+---------+---------+ 1020
         cggccttcactggaggttacgacgggagtgagacgccttgaaaacgttgaccgtcttcgt b        P   E   V   T   S   N   A   A   L   T   L   R   N   F   C   N   W   Q   K   Q    - gcacaacccacccagtgaccgggatgcagagcactatgacacagcaattcttttcaccag
   1021  ---------+---------+---------+---------+---------+---------+ 1080
         cgtgttgggtgggtcactggccctacgtctcgtgatactgtgtcgttaagaaaagtggtc b        H   N   P   P   S   D   R   D   A   E   H   Y   D   T   A   I   L   F   T   R    - acaggacttgtgtgggtcccagacatgtgatactcttgggatggctgatgttggaactgt
   1081  ---------+---------+---------+---------+---------+---------+ 1140
         tgtcctgaacacacccagggtctgtacactatgagaaccctaccgactacaaccttgaca b        Q   D   L   C   G   S   Q   T   C   D   T   L   G   M   A   D   V   G   T   V    - gtgtgatccgagcagaagctgctccgtcatagaagatgatggtttacaagctgccttcac
   1141  ---------+---------+---------+---------+---------+---------+ 1200
         cacactaggctcgtcttcgacgaggcagtatcttctactaccaaatgttcgacggaagtg b        C   D   P   S   R   S   C   S   V   I   E   D   D   G   L   Q   A   A   F   T    - cacagcccatgaattaggccacgtgtttaacatgccacatgatgatgcaaagcagtgtgc
   1201  ---------+---------+---------+---------+---------+---------+ 1260
         gtgtcgggtacttaatccggtgcacaaattgtacggtgtactactacgtttcgtcacacg b        T   A   H   E   L   G   H   V   F   N   M   P   H   D   D   A   K   Q   C   A    - cagccttaatggtgtgaaccaggattcccacatgatggcgtcaatgctttccaacctgga
   1261  ---------+---------+---------+---------+---------+---------+ 1320
         gtcggaattaccacacttggtcctaagggtgtactaccgcagttacgaaaggttggacct b        S   L   N   G   V   N   Q   D   S   H   M   M   A   S   M   L   S   N   L   D    -
```

FIG. 1iv

```
      ccacagccagccttggtctccttgcagtgcctacatgattacatcatttctggataatgg
 1321 ---------+---------+---------+---------+---------+---------+ 1380
      ggtgtcggtcggaaccagaggaacgtcacggatgtactaatgtagtaaagacctattacc b       H  S  Q  P  W  S  P  C  S  A  Y  M  I  T  S  F  L  D  N  G  - tcatggggaatgtttgatggacaagcctcagaatcccatacagctcccaggcgatctccc
 1381 ---------+---------+---------+---------+---------+---------+ 1440
      agtaccccttacaaactacctgttcggagtcttagggtatgtcgagggtccgctagaggg b       H  G  E  C  L  M  D  K  P  Q  N  P  I  Q  L  P  G  D  L  P  - tggcacctcgtacgatgccaaccggcagtgccagtttacatttggggaggactccaaaca
 1441 ---------+---------+---------+---------+---------+---------+ 1500
      accgtggagcatgctacggttggccgtcacggtcaaatgtaaaccccctcctgaggtttgt b       G  T  S  Y  D  A  N  R  Q  C  Q  F  T  F  G  E  D  S  K  H  - ctgccctgatgcagccagcacatgtagcaccttgtggtgtaccggcacctctggtggggt
 1501 ---------+---------+---------+---------+---------+---------+ 1560
      gacgggactacgtcggtcgtgtacatcgtggaacaccacatggccgtggagaccacccca b       C  P  D  A  A  S  T  C  S  T  L  W  C  T  G  T  S  G  G  V  - gctggtgtgtcaaaccaaacacttcccgtgggcggatggcaccagctgtggagaagggaa
 1561 ---------+---------+---------+---------+---------+---------+ 1620
      cgaccacacagtttggtttgtgaagggcacccgcctaccgtggtcgacacctcttccctt b       L  V  C  Q  T  K  H  F  P  W  A  D  G  T  S  C  G  E  G  K  - atggtgtatcaacggcaagtgtgtgaacaaaacccacagaaagcattttgatacgccttt
 1621 ---------+---------+---------+---------+---------+---------+ 1680
      taccacatagttgccgttcacacacttgttttgggtgtctttcgtaaaactatgcggaaa b       W  C  I  N  G  K  C  V  N  K  T  H  R  K  H  F  D  T  P  F  - tcatggaagctggggaatgtgggggccttggggagactgttcgagaacgtgcggtggagg
 1681 ---------+---------+---------+---------+---------+---------+ 1740
      agtaccttcgaccccttacaccccggaacccctctgacaagctcttgcacgccacctcc b       H  G  S  W  G  M  W  G  P  W  G  D  C  S  R  T  C  G  G  - agtccagtacacgatgagggaatgtgacaacccagtcccaaagaatggagggaagtactg
 1741 ---------+---------+---------+---------+---------+---------+ 1800
```

FIG. 1v

```
       tcaggtcatgtgctactcccttacactgttgggtcagggtttcttacctcccttcatgac
b       V  Q  Y  T  M  R  E  C  D  N  P  V  P  K  N  G  G  K  Y  C  - tgaaggcaaacgagtgcgctacagatcctgtaaccttgaggactgtccagacaataatgg
  1801 ---------+---------+---------+---------+---------+---------+ 1860
       acttccgtttgctcacgcgatgtctaggacattggaactcctgacaggtctgttattacc
b       E  G  K  R  V  R  Y  R  S  C  N  L  E  D  C  P  D  N  N  G  - aaaaacctttagagaggaacaatgtgaagcacacaacgagttttcaaaagcttcctttgg
  1861 ---------+---------+---------+---------+---------+---------+ 1920
       ttttttggaaatctctccttgttacacttcgtgtgttgctcaaaagttttcgaaggaaacc
b       K  T  F  R  E  E  Q  C  E  A  H  N  E  F  S  K  A  S  F  G  - gagtgggcctgcggtggaatggattcccaagtacgctggcgtctcaccaaaggacaggtg
  1921 ---------+---------+---------+---------+---------+---------+ 1980
       ctcacccggacgccaccttacctaagggttcatgcgaccgcagagtggtttcctgtccac
b       S  G  P  A  V  E  W  I  P  K  Y  A  G  V  S  P  K  D  R  C  - caagctcatctgccaagccaaaggcattggctacttcttcgttttgcagcccaaggttgt
  1981 ---------+---------+---------+---------+---------+---------+ 2040
       gttcgagtagacggttcggttttccgtaaccgatgaagaagcaaaacgtcgggttccaaca
b       K  L  I  C  Q  A  K  G  I  G  Y  F  F  V  L  Q  P  K  V  V  - agatggtactccatgtagcccagattccacctctgtctgtgtgcaaggacagtgtgtaaa
  2041 ---------+---------+---------+---------+---------+---------+ 2100
       tctaccatgaggtacatcgggtctaaggtggagacagacacacgttcctgtcacacattt
b       D  G  T  P  C  S  P  D  S  T  S  V  C  V  Q  G  Q  C  V  K  - agctggttgtgatcgcatcatagactccaaaaagaagtttgataaatgtggtgtttgcgg
  2101 ---------+---------+---------+---------+---------+---------+ 2160
       tcgaccaacactagcgtagtatctgaggttttcttcaaactatttacaccacaaacgcc
b       A  G  C  D  R  I  I  D  S  K  K  K  F  D  K  C  G  V  C  G  - gggaaatggatctacttgtaaaaaaatatcaggatcagttactagtgcaaaacctggata
  2161 ---------+---------+---------+---------+---------+---------+ 2220
       ccctttacctagatgaacatttttttatagtcctagtcaatgatcacgttttggacctat
```

FIG. 1vi

```
b         G  N  G  S  T  C  K  K  I  S  G  S  V  T  S  A  K  P  G  Y  - tcatgatatcatcacaattccaactggagccaccaacatcgaagtgaaacagcggaacca
    2221  ---------+---------+---------+---------+---------+---------+  2280
          agtactatagtagtgttaaggttgacctcggtggttgtagcttcactttgtcgccttggt b         H  D  I  I  T  I  P  T  G  A  T  N  I  E  V  K  Q  R  N  Q  - gaggggatccaggaacaatggcagctttcttgccatcaaagctgctgatggcacatatat
    2281  ---------+---------+---------+---------+---------+---------+  2340
          ctcccctaggtccttgttaccgtcgaaagaacggtagtttcgacgactaccgtgtatata b         R  G  S  R  N  N  G  S  F  L  A  I  K  A  A  D  G  T  Y  I  - tcttaatggtgactacactttgtccaccttagagcaagacattatgtacaaaggtgttgt
    2341  ---------+---------+---------+---------+---------+---------+  2400
          agaattaccactgatgtgaaacaggtggaatctcgttctgtaatacatgtttccacaaca b         L  N  G  D  Y  T  L  S  T  L  E  Q  D  I  M  Y  K  G  V  V  - cttgaggtacagcggctcctctgcggcattggaaagaattcgcagctttagccctctcaa
    2401  ---------+---------+---------+---------+---------+---------+  2460
          gaactccatgtcgccgaggagacgccgtaaccttcttaagcgtcgaaatcgggagagtt b         L  R  Y  S  G  S  S  A  A  L  E  R  I  R  S  F  S  P  L  K  - agagcccttgaccatccaggttcttactgtgggcaatgcccttcgacctaaaattaaata
    2461  ---------+---------+---------+---------+---------+---------+  2520
          tctcgggaactggtaggtccaagaatgacacccgttacgggaagctggattttaatttat b         E  P  L  T  I  Q  V  L  T  V  G  N  A  L  R  P  K  I  K  Y  - cacctacttcgtaaagaagaagaaggaatctttcaatgctatccccactttttcagcatg
    2521  ---------+---------+---------+---------+---------+---------+  2580
          gtggatgaagcatttcttcttcttccttagaaagttacgatagggtgaaaaagtcgtac b         T  Y  F  V  K  K  K  K  E  S  F  N  A  I  P  T  F  S  A  W  - ggtcattgaagagtggggcgaatgttctaagtcatgtgaattgggttggcagagaagact
    2581  ---------+---------+---------+---------+---------+---------+  2640
          ccagtaacttctcaccccgcttacaagattcagtacacttaacccaaccgtctcttctga b         V  I  E  E  W  G  E  C  S  K  S  C  E  L  G  W  Q  R  R  L  -
```

FIG. 1vii

```
         ggtagaatgccgagacattaatggacagcctgcttccgagtgtgcaaaggaagtgaagcc
    2641 ---------+---------+---------+---------+---------+---------+ 2700
         ccatcttacggctctgtaattacctgtcggacgaaggctcacacgtttccttcacttcgg b       V  E  C  R  D  I  N  G  Q  P  A  S  E  C  A  K  E  V  K  P  - agccagcaccagaccttgtgcagaccatccctgcccccagtggcagctggggagtggtc
    2701 ---------+---------+---------+---------+---------+---------+ 2760
         tcggtcgtggtctggaacacgtctggtagggacggggtcaccgtcgaccccctcaccag b       A  S  T  R  P  C  A  D  H  P  C  P  Q  W  Q  L  G  E  W  S  - atcatgttctaagacctgtgggaagggttacaaaaaaagaagcttgaagtgtctgtccca
    2761 ---------+---------+---------+---------+---------+---------+ 2820
         tagtacaagattctggacacccttcccaatgttttttcttcgaacttcacagacaggt b       S  C  S  K  T  C  G  K  G  Y  K  K  R  S  L  K  C  L  S  H  - tgatggaggggtgttatctcatgagagctgtgatcctttaaagaaacctaaacatttcat
    2821 ---------+---------+---------+---------+---------+---------+ 2880
         actacctccccacaatagagtactctcgacactaggaaatttctttggatttgtaaagta b       D  G  G  V  L  S  H  E  S  C  D  P  L  K  K  P  K  H  F  I  - agacttttgcacaatggcagaatgcagttaagtggtttaagtggtgttagctttgagggc
    2881 ---------+---------+---------+---------+---------+---------+ 2940
         tctgaaaacgtgttaccgtcttacgtcaattcaccaaattcaccacaatcgaaactcccg b       D  F  C  T  M  A  E  C  S  *                                - aaggcaaagtgaggaagggctggtgcagggaaagcaagaaggctggagggatccagcgta
    2941 ---------+---------+---------+---------+---------+---------+ 3000
         ttccgtttcactccttcccgaccacgtccctttcgttcttccgacctccctaggtcgcat tcttgccagtaaccagtgaggtgtatcagtaaggtgggattatgggggtagatagaaaag
    3001 ---------+---------+---------+---------+---------+---------+ 3060
         agaacggtcattggtcactccacatagtcattccaccctaataccccatctatctttc gagttgaatcatcagagtaaactgccagttgcaaatttgataggatagttagtgaggatt
    3061 ---------+---------+---------+---------+---------+---------+ 3120
         ctcaacttagtagtctcatttgacggtcaacgtttaaactatcctatcaatcactcctaa attaacctctgagcagtgatatagcataataaagccccgggcattattattattatttct
```

FIG. 1viii

```
3121 ----------+---------+---------+---------+---------+---------+ 3180
     taattggagactcgtcactatatcgtattatttcggggcccgtaataataataataaaga tttgttacatctattacaagtttagaaaaaacaaagcaattgtcaaaaaaagttagaact
3181 ----------+---------+---------+---------+---------+---------+ 3240
     aaacaatgtagataatgttcaaatcttttttgtttcgttaacagttttttttcaatcttga attacaaccctgtttcctggtacttatcaaaatacttaagtatcatgggggttgggaaa
3241 ----------+---------+---------+---------+---------+---------+ 3300
     taatgttggggacaaaggaccatgaatagttttatgaattcatagtaccccaacccttt tgaaaagtaggagaaaagtgagattttacttaagacctgttttactttaccttcactaac
3301 ----------+---------+---------+---------+---------+---------+ 3360
     acttttcatcctcttttcactctaaaatgaattctggacaaaatgaaatggaagtgattg aatgggggagaaaggagtacaaataggatctttgaccagcactgtttatggctgctatg
3361 ----------+---------+---------+---------+---------+---------+ 3420
     ttaccccctcttcctcatgtttatcctagaaactggtcgtgacaaataccgacgatac gtttcagagaatgtttatacattatttctaccgagaattaaaacttcagattgttcaaca
3421 ----------+---------+---------+---------+---------+---------+ 3480
     caaagtctcttacaaatatgtaataaagatggctcttaattttgaagtctaacaagttgt tgagagaaaggctcagcaacgtgaaataacgcaaatggcttcctctttcctttttggac
3481 ----------+---------+---------+---------+---------+---------+ 3540
     actctctttccgagtcgttgcactttattgcgtttaccgaaggagaaaggaaaaaacctg catctcagtctttatttgtgtaattcattttgaggaaaaaacaactccatgtatttattc
3541 ----------+---------+---------+---------+---------+---------+ 3600
     gtagagtcagaaataaacacattaagtaaaactccttttttgttgaggtacataaataag aagtgcattaaagtctacaatggaaaaaaagcagtgaagcattagatgctggtaaaagct
3601 ----------+---------+---------+---------+---------+---------+ 3660
     ttcacgtaatttcagatgttacctttttttcgtcacttcgtaatctacgaccattttcga agaggagacacaatgagcttagtacctccaacttcctttctttcctaccatgtaaccctg
3661 ----------+---------+---------+---------+---------+---------+ 3720
     tctcctctgtgttactcgaatcatggaggttgaaggaaagaaaggatggtacattgggac ctttgggaatatggatgtaaagaagtaacttgtgtctcatgaaaatcagtacaatcacac
```

FIG. 1ix

```
3721 ---------+---------+---------+---------+---------+---------+ 3780
     gaaacccttatacctacatttcttcattgaacacagagtacttttagtcatgttagtgtg aaggaggatgaaacgccggaacaaaaatgaggtgtgtagaacagggtcccacaggtttgg
3781 ---------+---------+---------+---------+---------+---------+ 3840
     ttcctcctactttgcggccttgttttta ctccacacatcttgtcccagggtgtccaaacc ggacattgagatcacttgtcttgtggtggggaggctgctgaggggtagc
3841 ---------+---------+---------+---------+--------- 3889
     cctgtaactctagtgaacagaacaccacccctccgacgactccccatcg
```

HUMAN AGGRECANASE AND NUCLEIC ACID COMPOSITIONS ENCODING THE SAME

CROSS REFERENCE TO RELATED APPLICATIONS

Pursuant to 35 U.S.C. §119 (e), this application claims priority to the filing date of the U.S. Provisional Patent Application Serial No. 60/133,343 filed May 10, 1999, the disclosure of which is herein incorporated by reference.

INTRODUCTION

1. Field of the Invention

The field of the invention is proteases, particularly proteases that cleave aggrecan.

2. Background of the Invention

Cartilage matrix structure as dry weight of the tissue is made up of 70% collagen and 20–30% proteoglycans. The proteoglycan component confers mechanical flexibility to load bearing tissues and imparts viscoelastic properties to cartilage. Its loss leads to rapid structural damage as is seen most frequently in arthritic joint diseases and joint injury.

Aggrecan is a major cartilage proteoglycan. Aggrecan is a large protein of 210 kDa and has three globular domains: G1, G2, and G3. The G1 and G2 domains of the protein are closer to the amino terminus of the protein and their intervening interglobular domain has sites that are proteolytically sensitive. The region between G2 and G3 is heavily glycosylated and connected to oligosaccharides and glycosaminoglycans (GAGs) to form the mature proteoglycan. In arthritic cartilage, core protein fragments of 55 kDa are observed and believed to be the result of cleavage of the core protein in the G1 and G2 interglobular domain between asparagine 341 and phenylalanine 342. This cleavage can be made by many matrix metalloproteinases e.g. MMP-1, -2, -3, -7, -8, -9, and -13. In addition, 60 kDa aggrecan fragments with a —COOH terminus of glutamic acid are also identified and are indicative of a cleavage site between glutamic acid 373 and alanine 374. Matrix metalloproteinase are unable to cleave at this site. The unique endopeptidase activity responsible for this cleavage has been termed "aggrecanase."

The G1 domain of the core protein forms a stable ternary complex by binding to hyaluronic acid and link proteins in the matrix. Any enzymatic cleavage in this region destabilizes the cartilage matrix structure, leads to the loss of the major proteoglycan aggrecan and exposes type II collagen to collagenases, causing cartilage loss and the consequent development of joint disease. Since a variety of anti-arthritic drugs do not target aggrecanase and are incapable of blocking cleavage of aggrecan, the aggrecanase site plays a key role in the proteolytic degradation of aggrecan.

As such, aggrecanase is considered to be an important drug target for arthritis. Aggrecan fragments released into the synovial fluid are the primary detectable events in the development of rheumatoid- and osteo-arthritis. Search for this protease has been intense. Despite these intense discovery efforts, identification of human aggrecanase has remained elusive.

As such, there is much interest in the identification of human aggrecanase, as well as the gene encoding this activity.

Relevant Literature

U.S. Patents of interest include: U.S. Pat. Nos. 5,872,209 and 5,427,954. PCT publications of interest include: WO 99/09000; WO 98/55643; WO 98/51665; and WO 97/18207.

Other references of interest include: Vankemmelbeke et al., "Coincubation of bovine synovial or capsular tissue with cartilage generates a soluble 'Aggrecanase' activity," Biochem Biophys Res Commun (Feb. 24, 1999) 255(3): 686–91; Arner et al., "Generation and Characterization of Aggrecanase. A soluble, cartilage-derived aggrecan-degrading activity," J Biol Chem (Mar. 5, 1999) 274(10): 6594–6601; Billington et al., "An aggrecan-degrading activity associated with chondrocyte membranes," Biochem J (Nov. 15, 1998) 336 (Pt 1):207–12; Hughes et al., "Differential expression of aggrecanase and matrix metalloproteinase activity in chondrocytes isolated from bovine and porcine articular cartilage," J Biol Chem (Nov. 13, 1998) 273(46):30576–82; Sandy et al., "Chondrocyte-mediated catabolism of aggrecan: aggrecanase-dependent cleavage induced by interleukin-1 or retinoic acid can be inhibited by glucosamine," Biochem J (Oct. 1, 1998) 335 (Pt 1):59–66; Arner et al., "Cytokine-induced cartilage proteoglycan degradation is mediated by aggrecanase," Osteoarthritis Cartilage (May 1998) 6(3):214–28; Ilic et al., "Characterization of aggrecan retained and lost from the extracellular matrix of articular cartilage. Involvement of carboxyl-terminal processing in the catabolism of aggrecan," J Biol Chem (Jul. 10, 1998) 273(28):17451–8; and Buttner et al., "Membrane type 1 matrix metalloproteinase (MT1-MMP) cleaves the recombinant aggrecan substrate rAgg1mut at the 'aggrecanase' and the MMP sites. Characterization of MT1-MMP catabolic activities on the interglobular domain of aggrecan," Biochem J (Jul. 1, 1998)333 (Pt 1):159–65.

SUMMARY OF THE INVENTION

Human aggrecanase and polypeptides related thereto, as well as nucleic acid compositions encoding the same, are provided. The subject polypeptide and nucleic acid compositions find use in a variety of applications, including research, diagnostic, and therapeutic agent screening applications, as well as in treatment therapies. Also provided are methods of treating disease conditions associated with aggrecanase activity, e.g. conditions characterized by the presence of aggrecan cleavage products, such as rheumatoid- and osteo-arthritis.

BRIEF DESCRIPTION OF THE FIGURES

FIG. 1 provides the nucleic acid (SEQ. ID. NO. 2) and amino acid (SEQ. ID. NO. 2) sequence of human aggrecanase.

DETAILED DESCRIPTION OF THE INVENTION

A novel human enzyme having aggrecan cleavage activity (i.e. human aggrecanase or ADAMTS-1) and polypeptides related thereto, as well as nucleic acid compositions encoding the same, are provided. The subject polypeptide and/or nucleic acid compositions find use in a variety of different applications, including research, diagnostic, and therapeutic agent screening/discovery/preparation applications. Also provided are methods of treating disease conditions associated with aggrecanase function, e.g. diseases characterized by the presence of aggrecan cleavage products, such as rheumatoid- and osteo-arthritis.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Polypeptide Compositions

A novel human enzyme having aggrecanase activity (i.e. human aggrecanase or ADAMTS-1), as well as polypeptide compositions related thereto, are provided. The term polypeptide composition as used herein refers to both the full length human protein, as well as portions or fragments thereof. Also included in this term are variations of the naturally occurring human protein, where such variations are homologous or substantially similar to the naturally occurring protein, as described in greater detail below. In the following description of the subject invention, the term "aggrecanase" is used to refer to the wild type human aggrecanase molecule of the subject invention.

The aggrecanase protein of the subject invention is an enzyme, particularly a proteinase and more particularly a metalloproteinase. The subject human aggrecanase is characterized by having aggrecanase activity. As such, the subject aggrecanase is capable of cleaving aggrecan in an interglobular domain, particularly between the G1 and G2 domains, and more particularly at the $Glu^{373}$-$Ala^{374}$ bond of human aggrecan, to produce a cleavage product having an N-terminal sequence of ARGSVIL.

Human aggrecanase has an amino acid sequence as shown in FIG. 1 and identified as SEQ ID NO:02. Human aggrecanase has a molecular weight based on its amino acid sequence of about 100 kDa. The true molecular weight of human aggrecanase may vary due to glycosylation and/or other postranslational modifications. As such, the actual molecular weight of human aggrecanase is likely to be in the range from about 80 to 100 kDa, usually from about 85 to 95 kDa.

Aggrecanase homologs or proteins (or fragments thereof) that vary in sequence from the wild type sequence of the subject invention are also provided. By homolog is meant a protein having at least about 35%, usually at least about 40% and more usually at least about 60% amino acid sequence identity to the human aggrecanase protein of the subject invention, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151–153. (Parameters used are ktuple 1, gpa penalty 3, window, 5 and diagonals saved 5).

Also provided are aggrecanase proteins that are substantially identical to the hu aggrecanase protein, where by substantially identical is meant that the protein has an amino acid sequence identity to the sequence of aggrecanase of at least about 60%, usually at least about 65% and more usually at least about 70%.

The proteins of the subject invention are present in a non-naturally occurring environment, e.g. are separated from their naturally occurring environment. In certain embodiments, the subject proteins are present in a composition that is enriched for the subject protein as compared to its naturally occurring environment. For example, purified aggrecanase is provided, where by purified is meant that the aggrecanase enzyme is present in a composition that is substantially free of non-aggrecanase proteins, where by substantially free is meant that less than 90%, usually less than 60% and more usually less than 50% of the composition is made up of non-aggrecanase proteins. The proteins of the subject invention may also be present as an isolate, by which is meant that the protein is substantially free of other proteins and other naturally occurring biologic molecules, such as oligosaccharides, polynucleotides and fragments thereof, and the like, where the term "substantially free" in this instance means that less than 70%, usually less than 60% and more usually less than 50% of the composition containing the isolated protein is some other naturally occurring biological molecule. In certain embodiments, the proteins are present in substantially pure form, where by "substantially pure form" is meant at least 95%, usually at least 97% and more usually at least 99% pure.

In addition to the naturally occurring proteins, polypeptides which vary from the naturally occurring proteins are also provided, e.g. aggrecanase polypeptides. By aggrecanase polypeptide is meant an amino acid sequence encoded by an open reading frame (ORF) of the gene encoding aggrecanase, described in greater detail below, including the full length aggrecanase protein and fragments thereof, particularly biologically active fragments and/or fragments corresponding to functional domains, e.g. transmembrane domain, and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length.

The subject proteins and polypeptides may be obtained from naturally occurring sources or synthetically produced. For example, human aggrecanase may be derived from biological sources which express aggrecanase, such as synoviocytes, chondrocytes, cartilege and the like. The subject proteins may also be derived from synthetic means, e.g. by expressing a recombinant gene encoding protein of interest in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source, e.g. chondrocytes or the expression host, and purified using HPLC, exclusion chromatography, gel electrophoresis, affinity chrornatography, and the like.

Nucleic Acid Compositions

Also provided are nucleic acid compositions encoding aggrecanase proteins or fragments thereof, as well as the aggrecanase homologues of the present invention. By aggrecanase nucleic acid composition is meant a composition comprising a sequence of DNA having an open reading frame that encodes aggrecanase, i.e. an aggrecanase gene, and is capable, under appropriate conditions, of being expressed as aggrecanase. Also encompassed in this term are nucleic acids that are homologous or substantially similar or identical to the nucleic acids encoding aggrecanase proteins. Thus, the subject invention provides genes encoding the human aggrecanase of the subject invention and homologs thereof. The human aggrecanase gene has the nucleic acid sequence shown in FIG. 1 and identified as SEQ ID NO:01, infra.

The source of homologous genes may be any species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J Mol. Biol.* 215:403–10 (using default settings, i.e. parameters w=4 and T=17). The sequences provided herein are essential for recognizing aggrecanase-related and homologous proteins, and the nucleic acids encoding the same, in database searches.

Nucleic acids encoding the aggrecanase protein and aggrecanase polypeptides of the subject invention may be cDNA or genomic DNA or a fragment thereof. The term "aggrecanase gene" shall be intended to mean the open reading frame encoding specific aggrecanase proteins and polypeptides, and aggrecanase introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding an aggrecanase protein.

A genomic sequence of interest comprises the nucleic acid present between the initiation codon and the stop codon, as defined in the listed sequences, including all of the introns that are normally present in a native chromosome. It may further include 5' and 3' un-translated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject aggrecanase protein. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The aggrecanase genes are isolated and obtained in substantial purity, generally as other than an intact chromosome. Usually, the DNA will be obtained substantially free of other nucleic acid sequences that do not include an aggrecanase sequence or fragment thereof, generally being at least about 50%, usually at least about 90% pure and are typically "recombinant", i.e. flanked by one or more nucleotides with which it is not normally associated on a naturally occurring chromosome.

Preparation of Aggrecanase Polypeptides

In addition to the plurality of uses described in greater detail in following sections, the subject nucleic acid compositions find use in the preparation of all or a portion of the aggrecanase polypeptides, as described above. The provided polynucleotide (e.g., a polynucleotide having a sequence of SEQ ID NO:01, the corresponding cDNA, or the full-length gene is used to express a partial or complete gene product. Constructs of polynucleotides having a sequences of "SEQ ID NO:01 can be generated synthetically. Alternatively, single-step assembly of a gene and entire plasmid from large numbers of oligodeoxyribonucleotides is described by, e.g., Stemmer et al., *Gene (Amsterdam)* (1995) 164(1):49–53. In this method, assembly PCR (the synthesis of long DNA sequences from large numbers of oligodeoxyribonucleotides (oligos)) is described. The method is derived from DNA shuffling (Stemmer, *Nature* (1994) 370:389–391), and does not rely on DNA ligase, but instead relies on DNA polymerase to build increasingly longer DNA fragments during the assembly process. Appropriate polynucleotide constructs are purified using standard recombinant DNA techniques as described in, for example, Sambrook et al., *Molecular Cloning: A Laboratory Manual*, 2nd Ed., (1989) Cold Spring Harbor Press, Cold Spring Harbor, N.Y., and under current regulations described in United States Dept. of HHS, National Institute of Health (NIH) Guidelines for Recombinant DNA Research.

Polynucleotide molecules comprising a polynucleotide sequence provided herein are propagated by placing the molecule in a vector. Viral and non-viral vectors are used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucieotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. The gene product encoded by a polynucleotide of the invention is expressed in any convenient expression system, including, for example, bacterial, yeast, insect, amphibian and mammalian systems. Suitable vectors and host cells are described in U.S. Pat. No. 5,654,173. In the expression vector, an aggrecanase encoding polynucleotide, e.g. as set forth in SEQ ID NO:01, is linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific or developmental stage-specific promoters. These are linked to the desired nucieotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the aggrecanase gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

Aggrecanase proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, HEK 293, CHO, Xenopus Oocytes, etc., may be used as the expression host cells. In some situations, it is desirable to express the aggrecanase gene in eukaryotic cells, where the aggrecanase protein will benefit from native folding and post-translational modifications. Small peptides can also be synthesized in the laboratory. Polypeptides that are subsets of the complete aggrecanase sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21–25; and Siebenlist et al., *Cell* (1980) 20:269.

Yeast. Expression systems in yeast include those described in Hinnen et al., *Proc. Natl. Acad Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci.* (*USA*) (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Pat. No. Re. 30,985.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject aggrecanase proteins without manipulation of the encoding nucleic acid itself, but instead through integration of a regulatory sequence into the genome of cell that already includes a gene encoding the desired protein, as is described in the above incorporated patent documents.

Uses of the Subject Aggrecanase Polypeptide and Nucleic Acid Compositions

The subject polypeptide and nucleic acid compositions find use in a variety of different applications, including research, diagnostic, and therapeutic agent screening/ discovery/preparation applications, as well as in therapeutic compositions and methods employing the same.

Research Applications

The subject nucleic acid compositions find use in a variety of research applications. Research applications of interest include: the identification of aggrecanase homologs; as a source of novel promoter elements; the identification of aggrecanase expression regulatory factors; as probes and primers in hybridization applications, e.g. PCR; the identification of expression patterns in biological specimens; the preparation of cell or animal models for aggrecanase function; the preparation of in vitro models for aggrecanase function; etc.

Homologs of the aggrecanase gene are identified by any of a number of methods. A ragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 Msodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/0 1.5 mM sodium citrate). Nucleic acids having a region of substantial identity to the provided aggrecanase sequences, e.g. allelic variants, genetically altered versions of the gene, etc., bind to the provided aggrecanase sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where aggrecanase is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of aggrecanase gene expression, especially in different tissues or stages of development, and to identify cis acting sequences and trans-acting factors that regulate or mediate aggrecanase gene expression. Such transcription or translational control regions may be operably linked to an aggrecanase gene in order to promote expression of wild type or altered aggrecanase or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section.

For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of aggrecanase gene expression in the sample.

The sequence of an aggrecanase gene, including flanking promoter regions and coding regions, may be mutated in various ways known in the art to generate targeted changes in promoter. strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of aggrecanase, or to alter properties of the protein that affect its function or regulation.

The subject nucleic acids can be used to generate transgenic, non-human animals or site specific gene modifications in cell lines. Transgenic animals may be made through homologous recombination, where the endogenous aggrecanase locus is altered. Alternatively, a nucleic acid construct is randomly integrated into the genome. Vectors for stable integration include plasmids, retroviruses and other animal viruses, YACs, and the like.

The modified cells or animals are useful in the study of aggrecanase function and regulation. Of interest is the use of aggrecanase genes to construct transgenic animal models of aggrecanase related disease conditions, e.g. disease conditions associated with aggrecanase activity, such as arthritis. Thus, transgenic animal models of the subject invention include endogenous aggrecanase knockouts in which expression of endogenous aggrecanase is at least reduced if not eliminated, where such animals also typically express an aggrecanase peptide of the subject invention, e.g. the aggrecanase protein of the subject invention or a fragment thereof. Where a nucleic acid having a sequence found in the human aggrecanase gene is introduced, the introduced nucleic acid may be either a complete or partial sequence of the aggrecanase gene. A detectable marker, such as lac Z may be introduced into the aggrecanase locus, where upregulation of aggrecanase expression will result in an easily detected change in phenotype. One may also provide for expression of the aggrecanase gene or variants thereof in cells or tissues where it is not normally expressed, at levels not normally present in such cells or tissues.

DNA constructs for homologous recombination will comprise at least a portion of the aggrecanase gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on aggrecanase activity.

Diagnostic Applications

Also provided are methods of diagnosing disease states based on observed levels of aggrecanase or the expression level of the aggrecanase gene in a biological sample of interest. Samples, as used herein, include biological fluids such as blood, cerebrospinal fluid, tears, saliva, lymph, dialysis fluid, and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal aggrecanase in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of aggrecanase. Biochemical studies may be performed to determine whether a sequence polymorphism in an aggrecanase coding region or control regions is associated with disease. Disease associated polymorphisms may include deletion or truncation of the gene, mutations that alter expression level, that affect the activity of the protein, etc.

Changes in the promoter or enhancer sequence that may affect expression levels of aggrecanase can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express aggrecanase may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J Hum. Genet.* 58:1239–1246.

A detectable label may be included in an amplification reaction. Suitable labels include fluorochromes, e.g fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type aggrecanase gene sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in aggrecanase may be based on the functional or antigenic characteristics of the protein. Protein truncation assays are useful in detecting deletions that may affect the biological activity of the protein. Various immunoassays designed to detect polymorphisms in aggrecanase proteins may be used in screening. Where many diverse genetic mutations lead to a particular disease phenotype, functional protein assays have proven to be effective screening tools. The activity of the encoded aggrecanase protein may be determined by comparison with the wild-type protein.

Diagnostic methods of the subject invention in which the level of aggrecanase gene expression is of interest will typically involve comparison of the aggrecanase nucleic acid abundance of a sample of interest with that of a control value to determine any relative differences, where the difference may be measured qualitatively and/or quantitatively, which differences are then related to the presence or absence of an abnormal aggrecanase gene expression pattern. A variety of different methods for determine the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The subject aggrecanase polypeptides find use in various screening assays designed to identify therapeutic agents. In vitro screening assays can be employed in which the activity of aggrecanase is assessed the presence of a candidate therapeutic agent and compared to a control, i.e. the activity in the absence of the candidate therapeutic agent. Activity can be determined in a number of different ways, where activity may generally be determined as ability to cleave aggrecan or at least a fragment therefore, as well as a recombinant polypeptide, that includes the aggrecanase cleavage site, as described above. Such assays are described in U.S. Pat. No. 5,872,209 and WO 99/05921, the disclosures of which are herein incorporated by reference, as well as Arner et al., J. Biol. Chem. (March 1999) 274: 6594–6601.

Also of interest in screening assays are non-human transgenic animals which express functional aggrecanase, where such animals are described above. In many embodiments, the animals lack endogenous aggrecanase. In using such animals for screening applications, a test compound(s) is administered to the animal, and the resultant changes in phenotype, e.g. presence of aggrecan produced by cleavage of the $Glu^{373}$-$Ala^{374}$ bond, are compared with a control.

Alternatively, in vitro models of aggrecanase binding activity may be measured in which binding events between aggrecanase and candidate aggrecanase modulatory agents are monitored.

A variety of other reagents may be included in the screening assays, depending on the particular screening protocols employed. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate therapeutic agents that serve as either aggrecanase agonists or antagonists may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Of particular interest in many embodiments are screening methods that identify agents that selectively modulate, e.g. inhibit, the subject aggrecanase enzyme and not other proteases.

Aggrecanase Nucleic Acid and Polypeptide Therapeutic Compositions

The nucleic acid compositions of the subject invention also find use as therapeutic agents in situations where one wishes to enhance aggrecanase activity in a host. The aggrecanase genes, gene fragments, or the encoded aggrecanase protein or protein fragments are useful in gene therapy to treat disorders associated with aggrecanase defects. Expression vectors may be used to introduce the aggrecanase gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day,.more usually for a period of at least about several days to several weeks.

The gene or aggrecanase protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Methods of Modulating Aggrecanase Activity

The subject invention provides methods of modulating aggrecanase activity in a cell, including methods of increasing aggrecanase activity (e.g. methods of enhancing ), as well as methods of reducing or inhibiting aggrecanase activity, e.g. methods of stopping or limiting aggrecan cleavage. In such methods, an effective amount of an aggrecanase modulatory agent is contacted with the cell.

Also provided are methods of modulating, including enhancing and inhibiting, aggrecanase activity in a host. In such methods, an effective amount of active agent that modulates the activity of aggrecanase in vivo, e.g. usually enhances or inhibits aggrecanase activity, is administered to the host. The active agent may be a variety of different compounds, including a naturally occurring or synthetic small molecule compound, an antibody, fragment or derivative thereof, an antisense composition, and the like.

Of particular interest in certain embodiments are agents that reduce aggrecanase activity, e.g. aggrecan cleavage, by at least about 10 fold, usually at least about 20 fold and more usually at least about 25 fold, as measure by the Assay described in Arner et al. (1999), supra. In many embodiments, of particular interest is the use of compounds that reduce aggrecanase activity by at least 100 fold, as compared to a control.

Also of interest is the use of agents that, while providing for reduced aggrecanase activity, do not substantially reduce the activity of other proteinases, if at all. Thus, the agents in this embodiment are selective inhibitors of aggrecanase. An agent is considered to be selective if it provides for the above reduced aggrecanase activity, but substantially no reduced activity of at least one other proteinase, where substantially no means less than 10 fold reduction, usually less than 5 fold reduction and in many instances less than 1 fold reduction, where activity is measured as described in Arner et al., (1999), supra.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically Include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Also of interest as active agents are antibodies that at least reduce, if not inhibit, the target aggrecanase activity in the host. Suitable antibodies are obtained by immunizing a host animal with peptides comprising all or a portion of the target protein, e.g. aggrecanase. Suitable host animals include mouse, rat sheep, goat, hamster, rabbit, etc. The origin of the protein immunogen may be mouse, human, rat, monkey etc. The host animal will generally be a different species than the immunogen, e.g. human aggrecanase used to immunize mice, etc.

The immunogen may comprise the complete protein, or fragments and derivatives thereof. Preferred immunogens comprise all or a part of aggrecanase, where these residues contain the post-translation modifications, such as glycosylation, found on the native target protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil & water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using aggrecanase bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 30 4,683,195 and 4,683, 202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG 1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of the gene encoding the target protein in the host. For example, antisense molecules can be used to down-regulate expression of aggrecanase in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation. Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5- propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

As mentioned above, an effective amount of the active agent is administered to the host, where "effective amount" means a dosage sufficient to produce a desired result. Generally, the desired result is at least an enhancement or reduction in aggrecanase activity, as measured by aggrecan cleavage product production, as compared to a control.

In the subject methods, the active agent(s) may be administered to the host using any convenient means capable of resulting in the desired modulation of aggrecanase activity, e.g. desired reduction in aggrecan cleavage product production. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the therapeutic DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving aggrecanase activity. Of particular interest is the use of the subject methods to treat disease conditions characterized by the presence of aggrecan cleavage products, particularly 60 kDa aggrecan cleavage products having an ARGS N-terminus. Specific diseases that are characterized by the presence of such methods include: rheumatoid arthritis, osteo-arthritis, infectious arthritis, gouty arthritis, psoriatic arthritis, spondolysis, sports injury, joint trauma, pulmonary disease, fibrosis, and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as hyperphosphatemia. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

A nucleic acid array carrying 699 known metalloprotein-ase genes and novel ESTs available in public and proprietary databases was designed. These sequences on the array were selected by a search with a seed set of known metalloprotease protein sequences from all species. These protein sequences were used to find matching sequences in human nucleotide databases (GenBank and LifeSeq) at the protein (codon) level. Redundant sequences were eliminated, remaining sequences assembled and clustered, and the unique set of 699 sequences were arrayed.

The resultant array was used to screen genes expressed in primary cultures of synoviocytes and chondrocytes. A fair number of metalloproteinases known to be expressed by these cells were identified. However, a number of ESTs for novel proteins were also identified. One of these ESTs was MPS5584x1. Upon further examination, this EST was found to be the human homolog of the murine ADAMTS-1, which has previously been cloned.

From the Incyte database, by homology search, we obtained other colinear human ESTs corresponding to the previously cloned mouse sequence. By synthesizing corresponding primers, the entire human ADAMTS cDNA was synthesized using PCR protocols. FIG. 1 provides the full length sequence of the human ADAMTS-cDNA (also referred to herein as human aggrecanase). An alignment analysis of this ADAMTS cDNA with the two ADMPs reported in WO 99/05291 (seq1 and seq2) and the novel metalloprotease reported in WO 97/31931 (w35293) was done using GAP (Needleman-Wunsch). (GAP program in GCG 10.0. A pairwise DNA alignment was made between each of the sequences; scoring matrix=PAM250. Gap and BestFit were originally written for Version 1.0 by Paul Haeberli from a careful reading of the Needleman and Wunsch (J. Mol. Biol. 48; 443–453 (1970)) and the Smith and Waterman (Adv. Appl. Math. 2; 482–489 (1981)) papers. Limited alignments were designed by Paul Haeberli and added to the Package for Versions 3.0. They were united into a single program by Philip Delaquess for Version 4.0).

The following results were obtained:

| Pairwise comparisons using Gap (Needleman-Wunsch), Matrix PAM250. | | | | |
| --- | --- | --- | --- | --- |
| | seq1 | seq2 | w35293 | |
| adamts1hum | 50% | 49% | 33% | (similarity) |
| | 38% | 39% | 15% | (identity) |
| seq1 | | 43% | 28% | |
| | | 32% | 19% | |
| seq2 | | | 35% | |
| | | | 18% | |

The human ADAMTS is clearly different from seq 1, seq2 and w35293.

It is apparent from the above results and discussion that human aggrecanase, as well as polypeptides related thereto and nucleic acid compositions encoding the same, are provided by the subject invention. These polypeptide and nucleic acid compositions find use in a variety of diverse applications, including research, diagnostic, screening and therapeutic applications. Also provided are novel methods of treating diseases associated aggrecanase, as the identification of the subject aggrecanase provides for an additional target for therapeutic agents for such diseases. Accordingly, the subject invention provides for a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A purified nucleic acid present in other than its natural environment, wherein said nucleic acid comprises a nucleotide sequence encoding an aggrecanase, and wherein the nucleotide sequence has the sequence set forth in SEQ ID NO:01.

2. An expression cassette comprising a transcriptional initiation region functional in an expression host, a nucleic acid according to claim 1 operably linked to said transcriptional initiation region, and a transcriptional termination region functional in said expression host.

3. An in vitro cell comprising an expression cassette according to claim 2 as part of an extrachromosomal element or integrated into the genome of a host cell as a result of introduction of said expression cassette into said host cell.

4. The cellular progeny of the host cell according to claim 2.

5. A method of producing aggrecanase in vitro, said method comprising:

culturing a cell according to claim 3, whereby said aggrecanase is expressed; and isolating said aggrecanase.

* * * * *

SEQUENCE LISTING

<160> NUMBER OF SEQ ID NOS: 2

<210> SEQ ID NO 1
<211> LENGTH: 3889
<212> TYPE: DNA
<213> ORGANISM: human

<400> SEQUENCE: 1

```
tgctccaatg cagcgatctg tgcccgaggg gttcggaagg cgcaagctgg gcagcgacat    60
ggggaacgcg gagcgggctc cggggtctcg gagctttggg cccgtaccca cgctgctgct   120
gctcgccgcg gcgctactgg ccgtgtcgga cgcactcggg cgcccctccg aggaggacga   180
ggagctagtg gtgccggagc tggagcgcgc cccgggacac gggaccacgc gcctccgcct   240
gcacgccttt gaccagcagc tggatctgga gctgcggccc gacagcagct ttttggcgcc   300
cggcttcacg ctccagaacg tggggcgcaa atccgggtcc gagacgccgc ttccggaaac   360
cgacctggcg cactgcttct actccggcac cgtgaatggc gatcccagct cggctgccgc   420
cctcagcctc tgcgagggcg tgcgcggcgc cttctacctg ctgggggagg cgtatttcat   480
ccagccgctg cccgccgcca gcgagcgcct cgccaccgcc gccccagggg agaagccgcc   540
ggcaccacta cagttccacc tcctgcgcgcg gaatcggcag ggcgacgtcg gcggcacgtg   600
cggggtcgtg gacgacgagc cccggccgac tgggaaagcg gagaccgaag acgaggacga   660
agggactgag ggcgaggacg aagggggctca gtggtcgccg caggacccgg cactgcaagg   720
cgtaggacag cccacaggaa ctggaagcat aagaaagaag cgatttgtgt ccagtcaccg   780
ctatgtggaa accatgcttg tggcagacca gtcgatggca gaattccacg gcagtggtct   840
aaagcattac cttctcacgt tgtttccggt ggcagccaga ttgtacaaac accccagcat   900
tcgtaattca gttagcctgg tggtggtgaa gatcttggtc atccacgatg aacagaaggg   960
gccggaagtg acctccaatg ctgccctcac tctgcggaac ttttgcaact ggcagaagca  1020
gcacaaccca cccagtgacc gggatgcaga gcactatgac acagcaattc tttttcaccag  1080
acaggacttg tgtgggtccc agacatgtga tactcttggg atggctgatg ttggaactgt  1140
gtgtgatccg agcagaagct gctccgtcat agaagatgat ggtttacaag ctgccttcac  1200
cacagcccat gaattaggcc acgtgtttaa catgccacat gatgatgcaa agcagtgtgc  1260
cagccttaat ggtgtgaacc aggattccca catgatggcg tcaatgcttt ccaacctgga  1320
ccacagccag ccttggtctc cttgcagtgc ctacatgatt acatcatttc tggataatgg  1380
tcatgggcaa tgtttgatgg acaagcctca gaatcccata cagctcccag gcgatctccc  1440
tggcacctcg tacgatgcca accggcagtg ccagtttaca tttggggagg actccaaaca  1500
ctgccctgat gcagccagca catgtagcac cttgtggtgt accggcacct ctggtgggggt  1560
gctggtgtgt caaaccaaac acttcccgtg ggcggatggc accagctgtg gagaagggaa  1620
atggtgtatc aacggcaagt gtgtgaacaa aacccacaga aagcattttg atacgccttt  1680
```

-continued

```
tcatggaagc tggggaatgt gggggccttg gggagactgt tcgagaacgt gcggtggagg    1740
agtccagtac acgatgaggg aatgtgacaa cccagtccca agaatggagg ggaagtactg    1800
tgaaggcaaa cgagtgcgct acagatcctg taaccttgag gactgtccag acaataatgg    1860
aaaaaccttt agagaggaac aatgtgaagc acacaacgag ttttcaaaag cttcctttgg    1920
gagtgggcct gcgtggaat ggattcccaa gtacgctggc gtctcaccaa aggacaggtg     1980
caagctcatc tgccaagcca aaggcattgg ctacttcttc gttttgcagc ccaaggttgt    2040
agatggtact ccatgtagcc cagattccac ctctgtctgt gtgcaaggac agtgtgtaaa    2100
agctggttgt gatcgcatca tagactccaa aaagaagttt gataaatgtg gtgtttgcgg    2160
gggaaatgga tctacttgta aaaaatatc aggatcagtt actagtgcaa aacctggata     2220
tcatgatatc atcacaattc caactggagc caccaacatc gaagtgaaac agcggaacca    2280 gagggatcc aggaacaatg gcagctttct tgccatcaaa gctgctgatg gcacatatat     2340
tcttaatggt gactacactt tgtccacctt agagcaagac attatgtaca aggtgttgt     2400 cttgaggtac agcggctcct ctgcggcatt ggaaagaatt cgcagcttta gccctctcaa    2460
agagcccttg accatccagg ttcttactgt gggcaatgcc cttcgaccta aaattaaata    2520
cacctacttc gtaaagaaga agaaggaatc tttcaatgct atccccactt tttcagcatg    2580
ggtcattgaa gagtggggcg aatgttctaa gtcatgtgaa ttgggttggc agagaagact    2640
ggtagaatgc cgagacatta atggacagcc tgcttccgag tgtgcaaagg aagtgaagcc    2700
agccagcacc agaccttgtg cagaccatcc ctgcccccag tggcagctgg gggagtggtc    2760
atcatgttct aagacctgtg ggaagggtta caaaaaaga agcttgaagt gtctgtccca    2820
tgatggaggg gtgttatctc atgagagctg tgatccttta agaaaccta aacatttcat     2880 agacttttgc acaatggcag aatgcagtta agtggtttaa gtggtgttag ctttgagggc    2940
aaggcaaagt gaggaagggc tggtgcaggg aaagcaagaa ggctggaggg atccagcgta    3000
tcttgccagt aaccagtgag gtgtatcagt aaggtgggat tatgggggta gatagaaaag    3060
gagttgaatc atcagagtaa actgccagtt gcaaatttga taggatagtt agtgaggatt    3120
attaacctct gagcagtgat atagcataat aaagccccgg gcattattat tattatttct    3180
tttgttacat ctattacaag tttagaaaaa acaaagcaat tgtcaaaaaa agttagaact    3240
attacaaccc ctgtttcctg gtacttatca aaatacttaa gtatcatggg ggttgggaaa    3300
tgaaaagtag gagaaaagtg agattttact taagacctgt tttactttac cttcactaac    3360
aatgggggga gaaaggagta caaataggat cttttgaccag cactgtttat ggctgctatg    3420
gtttcagaga atgtttatac attatttcta ccgagaatta aaacttcaga ttgttcaaca    3480
tgagagaaag gctcagcaac gtgaaataac gcaaatggct tcctctttcc tttttggac     3540 catctcagtc tttatttgtg taattcattt tgaggaaaaa acaactccat gtatttattc    3600
aagtgcatta aagtctacaa tggaaaaaaa gcagtgaagc attagatgct ggtaaaagct    3660
agaggagaca caatgagctt agtacctcca acttcctttc tttcctacca tgtaaccctg    3720
ctttgggaat atggatgtaa agaagtaact tgtgtctcat gaaaatcagt acaatcacac    3780
aaggaggatg aaacgccgga acaaaaatga ggtgtgtaga acagggtccc acaggtttgg    3840
ggacattgag atcacttgtc ttgtggtggg gaggctgctg aggggtagc                3889
```

<210> SEQ ID NO 2
<211> LENGTH: 949
<212> TYPE: PRT
<213> ORGANISM: human

```
<400> SEQUENCE: 2

Gly Asn Ala Glu Arg Ala Pro Gly Ser Arg Ser Phe Gly Pro Val Pro
 1               5                  10                  15

Thr Leu Leu Leu Leu Ala Ala Leu Leu Ala Val Ser Asp Ala Leu
             20                  25                  30

Gly Arg Pro Ser Glu Glu Asp Glu Glu Leu Val Val Pro Glu Leu Glu
             35                  40                  45

Arg Ala Pro Gly His Gly Thr Thr Arg Leu Arg Leu His Ala Phe Asp
 50                  55                  60

Gln Gln Leu Asp Leu Glu Leu Arg Pro Asp Ser Ser Phe Leu Ala Pro
65                  70                  75                  80

Gly Phe Thr Leu Gln Asn Val Gly Arg Lys Ser Gly Ser Glu Thr Pro
                 85                  90                  95

Leu Pro Glu Thr Asp Leu Ala His Cys Phe Tyr Ser Gly Thr Val Asn
                100                 105                 110

Gly Asp Pro Ser Ser Ala Ala Ala Leu Ser Leu Cys Glu Gly Val Arg
             115                 120                 125

Gly Ala Phe Tyr Leu Leu Gly Glu Ala Tyr Phe Ile Gln Pro Leu Pro
 130                 135                 140

Ala Ala Ser Glu Arg Leu Ala Thr Ala Ala Pro Gly Glu Lys Pro Pro
145                 150                 155                 160

Ala Pro Leu Gln Phe His Leu Leu Arg Arg Asn Arg Gln Gly Asp Val
                165                 170                 175

Gly Gly Thr Cys Gly Val Val Asp Asp Glu Pro Arg Pro Thr Gly Lys
             180                 185                 190

Ala Glu Thr Glu Asp Glu Asp Glu Gly Thr Glu Gly Glu Asp Glu Gly
             195                 200                 205

Ala Gln Trp Ser Pro Gln Asp Pro Ala Leu Gln Gly Val Gly Gln Pro
 210                 215                 220

Thr Gly Thr Gly Ser Ile Arg Lys Lys Arg Phe Val Ser Ser His Arg
225                 230                 235                 240

Tyr Val Glu Thr Met Leu Val Ala Asp Gln Ser Met Ala Glu Phe His
                245                 250                 255

Gly Ser Gly Leu Lys His Tyr Leu Leu Thr Leu Phe Ser Val Ala Ala
             260                 265                 270

Arg Leu Tyr Lys His Pro Ser Ile Arg Asn Ser Val Ser Leu Val Val
             275                 280                 285

Val Lys Ile Leu Val Ile His Asp Glu Gln Lys Gly Pro Glu Val Thr
 290                 295                 300

Ser Asn Ala Ala Leu Thr Leu Arg Asn Phe Cys Asn Trp Gln Lys Gln
305                 310                 315                 320

His Asn Pro Pro Ser Asp Arg Asp Ala Glu His Tyr Asp Thr Ala Ile
                325                 330                 335

Leu Phe Thr Arg Gln Asp Leu Cys Gly Ser Gln Thr Cys Asp Thr Leu
             340                 345                 350

Gly Met Ala Asp Val Gly Thr Val Cys Asp Pro Ser Arg Ser Cys Ser
             355                 360                 365

Val Ile Glu Asp Asp Gly Leu Gln Ala Ala Phe Thr Thr Ala His Glu
 370                 375                 380

Leu Gly His Val Phe Asn Met Pro His Asp Asp Ala Lys Gln Cys Ala
385                 390                 395                 400

Ser Leu Asn Gly Val Asn Gln Asp Ser His Met Met Ala Ser Met Leu
```

```
                    405                 410                 415
Ser Asn Leu Asp His Ser Gln Pro Trp Ser Pro Cys Ser Ala Tyr Met
                420                 425                 430
Ile Thr Ser Phe Leu Asp Asn Gly His Gly Glu Cys Leu Met Asp Lys
            435                 440                 445
Pro Gln Asn Pro Ile Gln Leu Pro Gly Asp Leu Pro Gly Thr Ser Tyr
        450                 455                 460
Asp Ala Asn Arg Gln Cys Gln Phe Thr Phe Gly Glu Asp Ser Lys His
465                 470                 475                 480
Cys Pro Asp Ala Ala Ser Thr Cys Ser Thr Leu Trp Cys Thr Gly Thr
                485                 490                 495
Ser Gly Gly Val Leu Val Cys Gln Thr Lys His Phe Pro Trp Ala Asp
                500                 505                 510
Gly Thr Ser Cys Gly Glu Gly Lys Trp Cys Ile Asn Gly Lys Cys Val
            515                 520                 525
Asn Lys Thr His Arg Lys His Phe Asp Thr Pro Phe His Gly Ser Trp
        530                 535                 540
Gly Met Trp Gly Pro Trp Gly Asp Cys Ser Arg Thr Cys Gly Gly Gly
545                 550                 555                 560
Val Gln Tyr Thr Met Arg Glu Cys Asp Asn Pro Val Pro Lys Asn Gly
                565                 570                 575
Gly Lys Tyr Cys Glu Gly Lys Arg Val Arg Tyr Arg Ser Cys Asn Leu
            580                 585                 590
Glu Asp Cys Pro Asp Asn Asn Gly Lys Thr Phe Arg Glu Glu Gln Cys
        595                 600                 605
Glu Ala His Asn Glu Phe Ser Lys Ala Ser Phe Gly Ser Gly Pro Ala
    610                 615                 620
Val Glu Trp Ile Pro Lys Tyr Ala Gly Val Ser Pro Lys Asp Arg Cys
625                 630                 635                 640
Lys Leu Ile Cys Gln Ala Lys Gly Ile Gly Tyr Phe Phe Val Leu Gln
                645                 650                 655
Pro Lys Val Val Asp Gly Thr Pro Cys Ser Pro Asp Ser Thr Ser Val
            660                 665                 670
Cys Val Gln Gly Gln Cys Val Lys Ala Gly Cys Asp Arg Ile Ile Asp
        675                 680                 685
Ser Lys Lys Lys Phe Asp Lys Cys Gly Val Cys Gly Gly Asn Gly Ser
    690                 695                 700
Thr Cys Lys Lys Ile Ser Gly Ser Val Thr Ser Ala Lys Pro Gly Tyr
705                 710                 715                 720
His Asp Ile Ile Thr Ile Pro Thr Gly Ala Thr Asn Ile Glu Val Lys
                725                 730                 735
Gln Arg Asn Gln Arg Gly Ser Arg Asn Asn Gly Ser Phe Leu Ala Ile
            740                 745                 750
Lys Ala Ala Asp Gly Thr Tyr Ile Leu Asn Gly Asp Tyr Thr Leu Ser
        755                 760                 765
Thr Leu Glu Gln Asp Ile Met Tyr Lys Gly Val Val Leu Arg Tyr Ser
    770                 775                 780
Gly Ser Ser Ala Ala Leu Glu Arg Ile Arg Ser Phe Ser Pro Leu Lys
785                 790                 795                 800
Glu Pro Leu Thr Ile Gln Val Leu Thr Val Gly Asn Ala Leu Arg Pro
                805                 810                 815
Lys Ile Lys Tyr Thr Tyr Phe Val Lys Lys Lys Glu Ser Phe Asn
            820                 825                 830
```

-continued

```
Ala Ile Pro Thr Phe Ser Ala Trp Val Ile Glu Glu Trp Gly Glu Cys
        835             840             845

Ser Lys Ser Cys Glu Leu Gly Trp Gln Arg Arg Leu Val Glu Cys Arg
    850             855             860

Asp Ile Asn Gly Gln Pro Ala Ser Glu Cys Ala Lys Glu Val Lys Pro
865             870             875             880

Ala Ser Thr Arg Pro Cys Ala Asp His Pro Cys Pro Gln Trp Gln Leu
            885             890             895

Gly Glu Trp Ser Ser Cys Ser Lys Thr Cys Gly Lys Gly Tyr Lys Lys
            900             905             910

Arg Ser Leu Lys Cys Leu Ser His Asp Gly Gly Val Leu Ser His Glu
        915             920             925

Ser Cys Asp Pro Leu Lys Lys Pro Lys His Phe Ile Asp Phe Cys Thr
    930             935             940

Met Ala Glu Cys Ser
945
```